US008025893B2

(12) United States Patent
Tas et al.

(10) Patent No.: US 8,025,893 B2
(45) Date of Patent: Sep. 27, 2011

(54) USE OF A SPECIFIC INHIBITOR OF HEDGEHOG/SMOOTHENED SIGNALING ON HYPERPIGMENTED SKIN TO OBTAIN DECREASE OF PIGMENTATION

(75) Inventors: Sinan Tas, Bor (TR); Oktay Avci, Izmir (TR)

(73) Assignee: Sinan Tas, Bor (TR)

( * ) Notice: Subject to any disclaimer, the term of this patent is extended or adjusted under 35 U.S.C. 154(b) by 659 days.

(21) Appl. No.: 11/874,631

(22) Filed: Oct. 18, 2007

(65) Prior Publication Data

US 2008/0089915 A1  Apr. 17, 2008

Related U.S. Application Data

(62) Division of application No. 10/682,584, filed on Oct. 9, 2003, now Pat. No. 7,893,078.

(51) Int. Cl.
*A61K 8/00* (2006.01)
*A61K 31/438* (2006.01)
(52) U.S. Cl. ............................ 424/401; 424/62; 514/278
(58) Field of Classification Search .................. 424/401, 424/62; 514/278
See application file for complete search history.

(56) References Cited

U.S. PATENT DOCUMENTS

| 4,370,322 | A | 1/1983 | Busse et al. |
| 6,291,516 | B1 | 9/2001 | Dudek et al. |
| 6,432,970 | B2 | 8/2002 | Beachy et al. |
| 6,951,839 | B1 | 10/2005 | Crompton |
| 2002/0165221 | A1 | 11/2002 | Baxter et al. |
| 2004/0072914 | A1 | 4/2004 | Tas et al. |

FOREIGN PATENT DOCUMENTS

| CA | 2416731 | | 1/2003 |
| KR | 2005037103 A | * | 4/2005 |
| WO | 9835020 | | 8/1998 |
| WO | 99/52534 | | 10/1999 |
| WO | 9952534 | | 10/1999 |
| WO | 0041545 | | 7/2000 |
| WO | 0074706 | | 12/2000 |
| WO | 01/27135 | | 4/2001 |
| WO | 0127135 A2 | | 4/2001 |
| WO | 0140438 A2 | | 6/2001 |
| WO | 0198344 | | 12/2001 |
| WO | 0207702 | | 1/2002 |
| WO | 0230462 | | 4/2002 |
| WO | 02080952 | | 10/2002 |

OTHER PUBLICATIONS

Jin, M. et al., "Skin whitening cosmetic composition containing jervine as active ingredient", KR 2005037103 A, Apr. 21, 2005, English abstract.*
Al-Suwaidan, S. N. et al., "Clearance is not a realistic expectation of psoriasis treatment", J Am Acad Dermatol, vol. 42, No. 5, Part 1, May 2000, pp. 796-802.

Ashcroft, D.M. et al., "Therapeutic strategies for psoriasis", Journal of Clinical Pharmacy and Therapeutics, 25, 2000, pp. 1-10.
Berman David M et al., Inhibition of prostate morphogensis by the Sonic hedgehog pathway inhibitor cyclopamine. The Journal of Urology, vol. 163, No. 4 Suppl., Apr. 2000, p. 204 XP008001018, 95th Annual Meeting of the American Urological Association, Inc.; Atlanta, Georgia, USA; Apr. 29, 2000-May 4, 1999 abstract.
Binns W. et al., "A Congenital Cyclopian-Type Malformation in Lambs Induced by Maternal Ingestion of a Rage Plat, *Veratrum californicum*", A.M. J. Vet. Res., Nov. 1963, 24, 103, pp. 1164-1175.
Bowman P.H. et al., "Combination of calcipotriene (Dovonex) ointment and tazarotene (Tazorac) gel versus clobetasol ointment in the treatment of plaque psoriasis: A pilot study", J. Am. Acad Dermatol, vol. 46, No. 6, Jun. 2002, pp. 907-913.
Cooper M.K. et al., "Teratogen-Mediated Inhibition of Target Tissue Response to Shh Signaling", Science, vol. 280, Jun. 5, 1998, pp. 1603-1607.
Detmer K. et al, "Erythroid differentiation in vitro is blocked by cyclopamine, an inhibitor of hedgehog signaling." Developmental Biology, vol. 222 No. 1, Jun. 1, 2000, p. 242 XP008001023, Fifty-ninth Annual Meeting of the Society for Development Biology; Boulder, Colorado, USA; Jun. 7-11, 2000, ISSN: 0012-1606 abstract.
Elder J.T. et al., "The Genetics of Psoriasis 2001 The Odyssey Continues", Arch Dermatol, vol. 137, Nov. 2001, pp. 1447-1454.
Goodrich L.V et al., "Hedgehog and Patched in Neural Development and Disease", Neuron, vol. 21, Dec. 1998, pp. 1243-1257.
Gottlieb S. L. et al., "Response of psoriasis to a lymphocyte-selective toxin (DAB398OL-2) suggest a primary immune, but not keratinocyte, pathogenic basis", Nature Medicine, vol. 1, No. 5, May 1995, pp. 442-447.
Incardona JP et al., "The teratogenic Veratrum alkaloid cyclopamine inhibits Sonic hedgehog signal transduction", Development 125, (1998), pp. 3553-3562.
Kanitakis J. et al., "Expression of the hair stem cell-specific keratin 15 in pilar tumors of the skin", European Journal of Dermatology, 1999, 9, pp. 363-365.
Keeler R.F. "Teratogenic Compounds of *Veratrum californicum* (Durand)—VI", Phytochemistry, vol. 8, (1969) pp. 223-225.
King L.E. et al., "Epidermal Growth Factor/Transforming Growth Factor Alpha Receptors and Psoriasis", The Society for Invesigative Dermatology, Inc., vol. 95, No. 5, Supplement, Nov. 1990, pp. 105-125.
Kooy AJ et al., Expression of E-Cadherin, a- & B-Catenin and CD44V6 and the Subcellular Localization of E-Cadherin and CD44V6 in Normal Epidermis and Basal Cell Carcinoma, Human Pathology, vol. 30, No. 11, Nov. 1999, pp. 1328-1335.
Krueger J.G., "The immunologic basis for the treatment of psoriasis with new biologic agents", J Am Acad Dematol, vol. 46, No. 1, Jan. 2002, pp. 1-23.
Lebwohl M. et al., "Treatment of psoriasis. Part 1. Topical therapy and phototherapy", J Am Acad Dermatol, vol. 45, No. 4, Oct. 2001, pp. 487-498.
Bollag, Wendy B., et al, "8-CL-Adenosine enahnces 1, 25-dihydroxyvitamin D3-induced growth inhibition without affecting 1, 25-dihydroxyvitamin D3-stimulated differentiation of primary mouse epidermal keratinocytes",BMC Pharmacology, 2004, 4:13.

(Continued)

*Primary Examiner* — Gina C Yu
(74) *Attorney, Agent, or Firm* — Vidas, Arrett & Steinkraus

(57) ABSTRACT

Cyclopamine or a similarly specific inhibitor of Hedgehog/Smoothened (Hh/Smo) signaling can be used for obtaining decrease of pigmentation of hyperpigmented skin areas.

4 Claims, No Drawings

OTHER PUBLICATIONS

Lyle S. et al., "The C8/144B monoclonal antibody recognizes cytokeratin 15 and defines the location of human hair follicle stem cells", Journal of Cell Science, 111, 1998, pp. 3179-3188.

Nickoloff B. J., "The Immunologic and Genetic Basis of Psoriasis", Arch Dermatol, vol. 135, Sep. 1999, pp. 1104-1110.

Outram S. V. et al., "Hedgehog Signaling Reglates Differentiation from Doble-Negative to Double-Positive Thymocyte", Immunity, vol. 13, Aug. 2000, pp. 187-197.

Spuls P. I. et al., "A systematic review of five systemic treatments for severe psoriasis", British Journal of Dermatology, 137, 1997, pp. 943-949.

Zhang Y. et al., "Hedgehog acts as a somatic stem cell factor in the Drosophila ovary", Nature, vol. 410, Mar. 29, 2001, pp. 599-604.

Levine, Edward M. et al., Sonic Hedgehog Promotes Rod Photoreceptor Differentiation in Mammalian Retinal Cells In Vitro, The Journal of Neuroscience, Aug. 15, 1997, 17(16):6277-6288.

Kim, Seung K. et al., "Pancreas development is promoted by cyclopamine, a Hedgehog signaling inhibitor," Proc. Natl. Acad. Sci. USA, vol. 95, pp. 13036-13041, Oct. 1998, Developmental Biology.

James P. Kutney et al, Synthesis Studies in the Veratrum Alkaloid Series, II. The Total Synthesis of Verarine, Veratramine, Jervine and Veratrobasine, Canadian J. Chemical, vol. 53, 1975, pp. 1796-1817.

Lu, X. et al "Loss of heterozygosity among tumor suppressor genes in invasive and in situ carcinoma of the uterine cervix", Int. J. Gynecol Cancer 2000, 10, pp. 452-458.

Fisher, Daniel et al, "Vertebrate HoxB gene expression requires DNA replication", European Molecular Biology Organization Journal, vol. 22, No. 14, pp. 373-3748, 2003.

Stenkamp, Deborah L., "Function for Hedgehog Genes in Zebrafish Retinal Development," Developmental Biology, vol. 220, pp. 238-252 (2000).

Treier, Mathias et al., "Hedgehog signaling is required for pituitary gland development," Development 128, pp. 377-386 (2001), Printed in Great Britain © The Company of Biologists Limited 2001.

Kahane, Nitza et al., "The third wave of myotome colonization by mitotically competent progenitors: regulating the balance between differentiation and proliferation during muscle development," Development 128, pp. 2187-2198 (2001), Printed in Great Britain © The Company of Biologists Limited 2001.

Fan, Hongran et al., "Sonic Hedgehog Opposes Epithelial Cell Cycle Arrest," The Journal of Cell Biology, vol. 147, No. 1, Oct. 4, 1999, pp. 71-76.

Sukegawa, Akiko et al., "The concentric structure of the developing gut is regulated by Sonic hedgehog derived from endodermal epithelium," Development 127, pp. 1971-1890 (2000), Printed in Great Britain © The Company of Biologists Limited 2000.

Zhang, Jian et al., "Downregulation of Hedgehog Signaling is Required for Organogenesis of the Small Intestine in Xenopus," Developmental Biology, vol. 229, pp. 188-202 (2001).

Van Den Brink, Gus R. et al., "Sonic Hedgehog Regulates Gastric Gland Morphogenesis in Man and Mouse," Gastroenterology, vol. 121, pp. 317-328 (2001).

Ramalho-Santos, Miguel et al., "Hedgehog signals regulate multiple aspects of gastrointestinal development," Development 127, pp. 2763-2772 (2000), Printed in Great Britain © The Company of Biologists Limited 2000.

Ishizuya-Oka, Atsuko et al., "Thyroid hormone-induced expression of Sonic hedgehog correlates with adult epithelial development during remodelling of the Xenopus stomach and intestine," Differentiation, vol. 69, pp. 27-37 (2001).

van den Brink, G.R. et al., "Sonic hedgehog expression correlates with fundic gland differentiation in the adult gastrointestinal tract," Gut, vol. 51, pp. 628-633 (2002).

Perron, Muriel et al., "A novel function for Hedgehog signaling in retinal pigment epithelium differentiation," Development 130, vol. 130, pp. 1565-1577, © 2003 The Company of Biologists Ltd.

Watkins, D. Neil et al., "Hedgehog signaling within airway epithelial progenitors and in small-cell lung cancer," Nature, vol. 422, pp. 313-317 (Mar. 20, 2003) © 2003 Nature Publishing Group.

Stenkamp, Deborah L., "Extraretinal and retinal hedgehog signaling sequentially regulate retinal differentiation in zebrafish," Departmental Biology, vol. 258, pp. 349-363 (2003) © 2003 Elsevier Science (USA).

Niemann, C. et al., "Indian hedgehog and β-catenin signaling: Role in the sebaceous lineage of normal and neoplastic mammalian epidermis," PNAS, vol. 100, Supplement 1, pp. 11873-11880 (Sep. 30, 2003).

Jarov, Artem et al., "A dual role for Sonic hedgehog in regulating adhesion and differentiation of neuroepithelial cells," Developmental Biology, vol. 261, pp. 520-536 (2003) © 2003 Elsevier Inc.

Allen, Mary et al., "Hedgehog Signaling Regulates Sebaceous Gland Development," American Journal of Pathology, vol. 163, No. 6, pp. 2173-2178 (Dec. 6, 2003) Copyright © American Society for Investigative Pathology.

Yao, Humphrey Hung-Chang et al., "Desert Hedgehog/Patched 1 signaling specifies fetal Leydig cell fate in testis organogenesis," Genes & Development, vol. 16, pp. 1433-1440 © 2002 by Cold Spring Harbor Laboratory Press.

Wang, Bu-er et al., "Inhibition of Epithelial Ductal Branching in the Prostate by Sonic Hedgehog is Indirectly Mediated by Stromal Cells," The Journal of Biological Chemistry, vol. 278, No. 20, pp. 18506-18513 (May 16, 2003) © 2003 by the American Society for Biochemistry and Molecular Biology, Inc.

Freestone, Sarah H. et al., "Sonic hedgehog regulates prostatic growth and epithelial differentiation," Developmental Biology, vol. 264, pp. 352-362 (2003).

Berman, David M. et al. "Widespread requirement for Hedgehog ligand stimulation in growth of digestive tract tumours," Nature, vol. 425, pp. 846-851 (Oct. 23, 2003).

Grachtchouk, Vladimir et al., "The magnitude of hedgehog signaling activity defines skin tumor phenotype," The EMBO Journal, vol. 22, No. 11, pp. 2741-2751 (2003).

Zhang, Yan et al., "Hedgehog acts as a somatic stem cell factor in the Drosophila ovary," Nature, vol. 410, pp. 599-604 (Mar. 29, 2001) © 2001 Macmillan Magazines Ltd.

Guenthner, ST et al.; "Cutaneous squamous cell carcinomas consistently show histologic evidence of in situ changes: A clinicopathologic correlation," J Am Acad Dermatol, vol. 41, No. 3, Part 1; Sep. 1999; pp. 443-448.

Hutchin, ME et al.; "Sustained Hedgehog signaling is required for basal cell carcinoma proliferation and survival: conditional skin tumorigenesis recapitulates the hair growth cycle" Genes & Development 2005 19:214-223.

Jackson, R. et al.; "Elderly and sun-affected skin" Can Fam Physician 2001;47:1236-1243.

Katsuura, M. et al.; "The NH2-terminal region of the active domain of sonic hedgehog is necessary for its signal transduction" FEBS Letters 447 (1999) 325-328.

Nasevicius, A. et al.; "Effective targeted gene 'knockdown' in zebrafish" Nature Genetics • vol. 26 • Oct. 2000; pp. 216-220.

Yashiro, K. et al.; "Actinic keratoses arising only on sun-exposed vitiligo skin" Clinical and Experimental Dermatology, 24, 199-201 (1999).

Yoshimura, M.D., K. et al.; "Usefulness of a Narrow-Band Reflectance Spectrophotometer in Evaluating Effects of Depigmenting Treatment" Aesth. Plast. Surg. 25:129-133, 2001.

Romer JT et al., "Suppression of the Shh pathway using a small molecule inhibitor eliminates medulloblastoma in Ptc1 +/-p53-/- mice" Cancer Cell: Sep. 2004 . vol. 6 . pp. 229-240.

Symmans WF et al., "Paclitaxel-induced Apoptosis and Mitotic Arrest Assessed by Serial Fine-Needle Aspiration: 2 Implications for Early Prediction of Breast Cancer Response to Neoadjuvant Treatment1" Clinical Cancer Research, vol. 6, 4610-4617, Dec. 2000.

van de Schepop, Ham et al., "Counting of apoptotic cells: a methodological study in invasive breast cancer" J Clin Pathol: Mol Pathol1996;49:M214-M217.

Vorechovsky, Igor et al, "Trichoepitheliomas Contain Somatic Mutations in the Overexpressed PTCH Gene: Support for a Gatekeeper Mechanism in Skin Tumorigenesis", Cancer Research 57, 4677-4681, Nov. 1, 1997.

Keeler, Richard F., "Teratogenic Effects of Cyclopamine and Jervine in Rats, Mice and Hamsters," Proceedings of the Society for Experimantal Biology and Medicine, vol. 149, pp. 302-306 (1975) Copyright © 1975 by the Society for Experimental Biology and Medicine.

Maesawa, Chihaya et al, "Mutations in the Human Homologue of the Drosophila Patched Gene in Esophageal Squamous Cell Carsinoma", Genes, Chromosones & Cancer 21:276-279, (1998).

Omnell, M.L. et al., "Expression of Veratrum Alkaloid Teratogenicity in the Mouse," Teratology, vol. 105-119 (1990).

Talpale Jussi et al., "Effects of oncogenic mutations in Smoothened and Patched can be reversed by cyclopamine," Nature, vol. 406, pp. 1005-1009 (Aug. 31, 2000) © 2000 Macmillan Magazines Ltd.

Xie, Jingwa et al, "Mutations of the PACTHED Gene in Several Types of SPoradic Extracutaneous Tumors", Cancer Research 57, pp. 2369-2372, Jun. 15, 1997.

Michimukai, Eiji et al., "Mutations in the Human Homologue of the Drosophila Segment Polarity Gene Patched in Oral Squamous Cell Carcinoma Cell Lines," In Vitro Cellular & Developmental Biology, vol. 37, No. 7, pp. 459-464 (Jul./Aug. 2001) ProQuest Medical Library.

Berman, David M. et al., "Medulloblastoma Growth Inhibition by Hedgehog Pathway Blockade," Science, vol. 297, pp. 1559-1561 (Aug. 30, 2002).

Thayer, Sarah P. et al., "Hedgehog is an early and late mediator of pancreatic cancer tumorigenesis," Nature, vol. 425, pp. 851-856 (Oct. 23, 2003).

Qualtrough, David et al., "Hedgehog Signalling in Colorectal Tumour Cells: Induction of Apoptosis with Cyclopamine Treatment," Int. J. Cancer, vol. 110, pp. 831-837 (2004) © 2004 Wiley-Liss, Inc.

Struhl, Gary et al, "Hedgehog organises the pattern and polarity of epidermal cells in the Drosophila abdomen", Development 124, 2143-2154 (1997).

Kimonis, V. E., "Clinical Manifestations in 105 Persons with Nevoid Basal Cell Carcinoma Syndrome", American Journal of Medical Genetics 69:299-308 (1997).

Goodman & Gilman's, The Pharmacological Basis of Therapeutics, Ninth Edition, (1996), Calabresi et al., Section X, Chemotherapy of Neoplastic Diseases, pp. 1225-1229.

Celso et al.,"Transient activation of B-catenin signaling in adult mouse epidermis is sufficient to induce new hair follicles but continuous activation is required to maintain hair follicle tumours," Development 131, 1787-1799, 2003.

Tas S et al, Induction of the differentiation and apoptosis of tumor cells in vivo with efficiency and selectivity. European Journal of Dermatology 2004; 14:96-102.

Riddle RD et al, Sonic hedgehog Mediates Polarizing Activity of the ZPA. Cell 1993; 75:1401-1416.

Basler K et al, Compartment boundaries and the control of Drosophila limb pattern by hedgehog protein. Nature 1994; 368: 208-214.

Kojima T et al, Induction of a mirror-image duplication of anterior wing structures by localized hedgehog expression in the anterior compartment of Drosophila melanogaster wing imaginal discs. Gene 1994; 148:211-217.

Heberlein U et al, Growth and differentiation in the Drosophila eye coordinated by hedgehog. Nature 1995; 373: 709-711.

Lepage T et al, "Signal transduction by cAMP-dependent protein kinase A in Drosophila limb patterning". Nature 1995; 373: 711-715.

Sanchez, Pilar et al, "In Vivo Inhibition of Endogenous Brain Tumors Through Systemic Interference of Hedgehog signaling in Mice", Mechanisms of Development, 122 (2005) pp. 223-230.

Bellusci S et al, "Involvement of Sonic hedgehog (Shh) in mouse embryonic lung growth and morphogenesis". Development 1997; 134: 53-63.

Litingtung Yet al, Sonic hedgehog is essential to foregut development. Nature Genetics 1998; 20: 58-61.

Orentas DM et al, "Sonic hedgehog signaling is required during the appearance of spinal cord oligodendrocyte precursors". Development 1999; 126:2419-2429.

Furumichi T et al, "Adenosine 3':5'-cyclic monophosphate inhibits in vitro angiogenesis induced by endothelial cell growth factor". Japanese Heart Journal 1992; 33: 373-382.

Tsopanoglou NE et al, "Opposing effects on modulation of angiogenesis by protein kinase C and cAMP-mediated pathways". Journal of Vascular Research 1994; 31: 195-204.

Johnson RL et al, "Patched overexpression alters wing disc size and pattern: transcriptional and post-transcriptional effects on hedgehog targets". Development 1995; 121: 4161-4170.

deCelis JF et al, "Ventral veinless, the gene encoding the Cf1a transcription factor, links positional information and cell differentiation during embryonic and imaginal development in Drosophila melanogaster". Development 1995; 121: 3405-3416.

Roberts D. J.et al, "Sonic hedgehog is an endodermal signal inducing Bmp-4 and Hox genes during induction and regionalization of the chick hindgut". Development 1995; 121: 3163-3174.

Winnier G et al, "Bone morphogenetic protein-4 is required for mesoderm formation and patterning in the mouse". Genes & Development 1995; 9: 2105-2116.

Bavik C et al, Developmental abnormalities in cultured mouse embryos deprived of retinoic acid by inhibition of yolk sac retinol binding protein synthesis. Proceedings of the National Academy of the Sciences o f USA 1996, 93: 3110-3114.

Dickson MC et al, Defective haematopoiesis and vasculogenesis in transforming growth factor-beta 1 knock out mice, Development 1995; 121: 1845-1854.

D'Angelo G et al, cAMP-dependent protein kinase inhibits the mitogenic action of vascular endothelial growth factor and fibroblast growth factor in capillary endothelial cells by blocking Raf activation. Journal of Cell Biochemistry 1997; 6767: 353-366.

Farrington SM et al, Winged-Helix, Hedgehog and Bmp genes are differentially expressed in distinct cell layers of the murine yolk sac. Mechanisms of Development 1997; 62: 197-211.

St Amand TR et al, Cloning and expression pattern of chicken Pitx2: A new component in the Shh signaling pathway controlling embryonic heart looping. Biochemical and Biophysical Research Communications 1998; 247: 100-105.

Pepicelli CV et al, Sonic hedgehog regulates branching morphogenesis in the mammalian lung. Current Biology 1998; 8: 1083-1086.

Grabel L et al, Using EC and ES cell culture to study early development: recent observations on Indian hedgehog and Bmps. International Journal of Developmental Biology 1998; 42: 917-925.

St Jacques B et al, Indian hedgehog signaling regulates proliferation and differentiation of chondrocytes and is essential for bone formation. Genes & Development 1999; 13: 2072-2086.

Brown LA et al, Insights into early vasculogenesis revealed by expression of the ETS-domain transcription factor Fli-1 in wild type and mutant zebrafish embryos. Mechanisms of Development 200; 90: 237-252, 2000.

Maye P et al, Indian hedgehog signaling in extraembryonic endoderm and ectoderm differentiation in ES embryoid bodies. Mechanisms of Development 2000; 94: 117-132.

Dyer M et al, Indian hedgehog activities hematopoiesis and vasculogenesis and can respecify prospective neuroectodermal cell fate in the mouse embryo. Development 2001; 128: 1717-1730.

Braybrooke JP et al, A phase II study of razoxane, an antiangiogenic topoisomerase II inhibitor, in renal cell cancer with assessment of potential surrogate markers of angiogenesis. Clinical Cancer Research 2000; 6: 4697-4704.

Dunn MK et al, Cyclopamine, A Steroidal Alkaloid Disrupts Development of Neural Crest Cells in Xenopus. Developmental Dynamics 1995; 202: 255-270.

Tas S et al, Rapid clearance of psoriatic skin lesions induced by topical cyclopamine. Dermatology 2004; 209: 126-131.

Sauder et al, Neovastat (AE-941), an inhibitor of angiogenesis: Randomized phase I/II clinical trial results in patients with plaque psoriasis. J Am Acad Dermatol; vol. 47, No. 4, 2002; 535-541.

Mimeault, Murielle, et al "Cytotoxic effects induced by a combination of cyclopamine and gefitinib, the selective hedgehog and epidermal growth factor receptor signaling in hibitors in prostate cancer cells", Int. J. Cancer: 118, 1022-1031 (2006).

Lebwohl Mark et al , "A randomized, double blind, placebo controlled study of clabetasol propionate 0.05% foam in the treatment of nonscalp psoriasis", International Journal of Dermatology, 2002, vol. 41, pp. 269-274.

"The Merk Manual of Diagnosis and Therapy" Merck Research Laboratories, 1999,p. 817.

Mohler J. et al "Activation of Knot (kn) Specifies the 3-4 Intervein Region in the Drosophila Wing". Development 2000:127:55-63.

Méthot et al.; "An absolute requirement for Cubitus interruptus in Hedgehog signaling" Development 128, 733-742 (2001).

Takimoto et al.; "Why Drugs Fail: Of Mice and Men Revisited" Clinical Cancer Research, vol. 7, 229-230, Feb. 2001.

Xu et al., "Genomewide Expression Profiling in the Zebrafish Embryo Identifies Target Genes Regulated by Hedgehog Signaling During Vertebrate Development" Genetics 2006; 174:735-752.

Nilsson M et al, "Induction of Basal Cell Carcinomas and Trichoephitheliomas in Mice Overexpressing GLI-1", Proc. Nat'l Acad. Sci. USA 2000; 97:3438-3443.

Stone, Donna M. et al, "The tumour-supressor gene patched encodes a candidate receptor for Sonic hedgehog", from Articles, 1996.

Suzuki, Hidekazu et al, "Down regulation of a morphogene(sonic hedgehog) gradient in the gastric epithelium of *Helicobacter pylori*-infected Mongolian gerbils", J. Pathol 2005: 206:187-197.

Sheng, Tao et al, "Activation of the hedgehog pathway in advanced prostate cancer", Molecular Cancer 2004, 3:29.

Kumamoto, Hiroyuki et al, "Expression of Sonic Hedgehog (SHH) signaling molecules in ameloblastomas", J. Oral Pathol Med (2004) 33: 185-190.

Xuan, Yan Hua et al, "Enhanced expression of hedgehog signaling molecules in squamous cell carcinoma of uterine cervix and it precursor lesions", Modern Pathology (2006) 19, 1139-1147.

Oliver, Trudy G., et al "Loss of patched and disruption of granule cell development in a pre-neoplastic stage of medulloblastoma", 2005.

Hannun, Yusuf A., BLOOD: Apoptosis and the Dilemma of Cancer Chemotherapy, The Journal of The American Society of Hematology, vol. 89, No. 6, Mar. 15, 1997, pp. 1845-1853.

Bijlsma, Maarten F., et al :Repression of Smoothened by Patched-Dependetn (Pro-) Vitamin D3 Secrettion, PloS Biology, Aug. 2006, vol. 4, Issue 8, pp. 1397-1410.

Dahmane, N. et al, "Activation of the Trnascription of factor Gli1 and the Sonic hedgehog signalling pathway in skin tumours", Nature, vol. 389, Oct. 23, 1997, pp. 876-881.

Williamham, Mark C., "Cytochemical Methods for the Detection of Apoptosis", The Hisochemical Society, Inc., vol. 47 (9), pp. 1101-1109, 1999.

Wicking, Carol et al "The Hedgehog Signalling Pathway in Tumorigenesis and Development", Oncogene (1999), vol. 18, pp. 7844-7851.

Hahn, Heidi et al, "The Patched Signaling Pathway in Tumorigeneis and Development: Lessons from Animal Models". J. Mol. Med (1999) vol. 77, pp. 459-468.

Kutney, James P. et al "Synthetic Studies in the veratrum Alkaloid Series II. The Total Synthesis of Verarine, Veratramine, Jervine and Veratrobasine", Can. J. Chem. vol. 53, 1975, pp. 1796-1817.

Krauss. S., et al "A functionally conserved homolog of the drosophila segment polarity gene hh is expressed in tissues with polarizing activity in zebrafish embryos",Cell vol. 75. pp. 1431-1444. Dec. 31, 1993.

Bellom, F. et al "Identification of Sonic hedgehog as a candidate gene responsible for holoprosencephaly", Nature Genetics vol. 14, Nov. 1996, pp. 353-356.

Roessler, Erich et al, "Mutations in the human Sonic Hedge hog gene cause holoprosencephaly", Nature Genetics, vol. 14, Nov. 1996, pp. 357-360.

Chiang, Chin, et al "Cyclopia and defective axial patterning in mice lacking Sonic Hedgehog gene function", Nature, vol. 383, Oct. 3, 1996, pp. 407-413.

Ericson, Johan et al "Two critical periods of sonic hedgehog signaling required for the specifciation of motor neuron identity", Cell. vol. 87, pp. 661-673, Nov. 15, 1996.

Chuang, Pao-Tien et al "Vertebrate hedgehog signalling modulated by induction of a hedgehog-binding protein" Nature vol. 397, Feb. 18, 1999, pp. 617-621.

Wang, Li Chun et al, "Conditional Disruption of Hedgehog Signaling Pathway Defines its Critical Role in Hair Development and Regeneration", The Journal of Investigative Dermatology, vol. 114, No. 5, May 2000, pp. 901-908.

Williams, Kevin P. et al "Functional antagonists of sonic hedgehog reveal the importance of the N terminus for activity". Journal of Cell Structure, vol. 112, (1999) pp. 4405-4414.

Bovenschen, H. J., et al, "Explorative immunohistochemical study of the evaluate the additional of a topical corticosteriod in the early phase of alefacept treatment for psoriasis", Arc Dermatol Res. (2007), 298: 457-463.

Gniadecki, Robert, "Effects of 1,25-dihydroxyvitamin D3 and its 20-epi analogues (MC 1288, MC 1301, KH 1060), on clonal keratinocyte growth: evidence for differentiation of keratinocyte stem cells and analysis of the modoculatory effects of cytokines". Britsh Journal of Pharmacology (1997) vol. 120, pp. 1119-1127.

Oro, Anthony E., et al "Basel Cell Carcinomas in Mice Overexpressing Sonic Hedgehog", Science, vol. 276, May 2, 1997, pp. 817-821.

Hopyan Seva et al "Indian Hedgehog and Parathyroid hormone related protein signaling in cartilage tumors of bone." Proceedings of the American Association for Cancer Research Annual, No. 41, Mar. 2000 p. 206 XP008001019, 91st Annual Meeting of the American Association for Cancer Research, San Francisco, CA, US, April Jan. 5, 2000, Mar. 2000, ISSN< 0197-016X Abstract.

Chen et al "Analysis of the zebrafish smoothened mutant reveals conserved and divergent functions of hedgehog activity", Development 128, 2385-2396 (2001).

* cited by examiner

USE OF A SPECIFIC INHIBITOR OF HEDGEHOG/SMOOTHENED SIGNALING ON HYPERPIGMENTED SKIN TO OBTAIN DECREASE OF PIGMENTATION

CROSS REFERENCE

This application is a division of application Ser. No. 10/682,584, filed Oct. 9, 2003.

BACKGROUND OF THE INVENTION

PCT/TR01/00027, filed 2 Jul. 2001, designating the United States and published as WO 02/078703; PCT/TR02/00017, filed 19 Apr. 2002, designating the United States and published as WO 02/078704; and U.S. application Ser. No. 10/682,584, filed 9 Oct. 2003, published as US 20040072914 A1, are each incorporated herein by reference in their entirety.

The gene patched-encodes a transmembrane protein acting as a receptor for the hedgehog proteins identified first by their effect on the patterning of tissues during development. When not liganded by hedgehog, the patched protein acts to inhibit intracellular signal transduction by another transmembrane protein, smoothened. Binding of hedgehog to the patched causes relieving of this inhibition. Intracellular signal transduction by the relieved smoothened then initiates a series of cellular events resulting ultimately in alterations of the expressions of the hedgehog target genes and of cellular behaviour. General features of this hedgehog/smoothened pathway of signal transduction, first identified in Drosophila, are conserved in diverse living organisms from Drosophila to Human. However, the pathway gets more complex in more advanced organisms (e.g. presence in human of more than one genes that display significant similarity to the single patched gene of Drosophila). Inactivating mutations of the patched have been found to cause constitutive (ligand-free) signaling through the hedgehog/smoothened pathway. The hedgehog/smoothened pathway overactivity, resulting from mutations of the patched and/or further downstream pathway elements, is found in all basal cell carcinomas (BCCs). The nevoid basal cell carcinoma syndrome (NBCCS) results from patched haplo insufficiency. Patients with the NBCCS, because of an already mutant patched in all cells, develop multiple BCC's as they grow older.

Hedgehog/smoothened signaling is known to be employed for normal functions in several normal tissues and for the maintenance of normal epithelial stem cells (Zhang Y et al (2001) Nature 410:599-604).

Cyclopamine, a steroid alkaloid, has the chemical formula shown below.

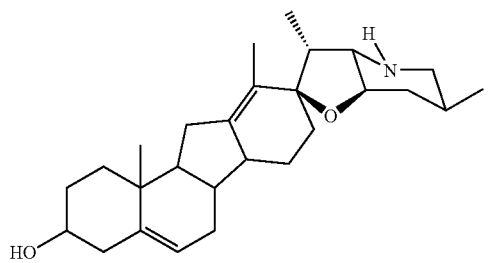

It is found naturally in the lily *Veratrum californicum* and can be obtained by purification from this and other sources. Teratogenicity of these plants on grazing pregnant animals led to the identification of cyclopamine as an active compound (Keeler R. F. (1969) Phytochemistry 8:223-225). How cyclopamine displayed teratogenicity was revealed by the finding that it is an inhibitor of the hedgehog/smoothened signal transduction pathway (Incardona J. P. et al. (1998) Development 125:3553-3562; Cooper M. K. et al. (1998) Science 280:1603-1607).

The sonic hedgehog protein, a member of the hedgehog family of proteins, has been found to induce differentiation of its target cells, including the precursors of ventral cells in the developing central nervous system (Goodrich L. V. et al. (1998) Neuron 21:1243-1257). Inhibition of the hedgehog/smoothened pathway by cyclopamine in the developing chicken brain prevented formation of the ventral cells and caused holoprosencephaly (Incardona J. P. et al. (1998) Development 125:3553-3562; Cooper M. K. et al. (1998) Science 280:1603-1607), the common malformation observed in the lambs of the sheep grazing Veratrum (Binns W. et al. (1963) Am. J. Vet. Res. 24:11641175). Cyclopamine has been reported to inhibit cellular differentiation in other systems as well, including the differentiation of bone marrow cells to erythroid cells (Detmer K. et al. (2000) Dev. Biol. 222:242) and the differentiation of the urogenital sinus to prostate (Berman D. M. et al. (2000) J. Urol. 163:204).

SUMMARY OF THE INVENTION

Cyclopamine or a similarly specific inhibitor of Hedgehog/Smoothened (Hh/Smo) signaling can be used for obtaining decrease of pigmentation of hyperpigmented skin areas. By applying a sufficient dosage, a hyperpigmented skin lesion can be caused to disappear. Besides having therapeutic utility, the method can provide an improvement in the appearance of skin and is useful for cosmetic purposes.

DETAILED DESCRIPTION OF THE INVENTION

As we show in detail in WO 02/078703 and US 2004/0072914 A1, treatment of human patients bearing skin tumors have shown that tumor cells can be induced to differentiate in vivo with efficiency and also with selectivity sparing adjacent normal tissue cells, including the normal cells having stem cell features. Achieved by use of a medicament comprising a specific inhibitor of Hh/Smo signaling, these effects were sensitive to the dosage of medicament and a massive apoptosis of the differentiating tumor cells was obtained by appropriately increased doses. The same investigations have demonstrated that a dosage of medicament sufficing to cause inhibition of tumor cell proliferation is insufficient to cause differentiation and apoptosis of the tumor cells and that the latter requires higher doses. It was further demonstrated that a cessation of tumor cell proliferation in vivo can be obtained as a consequence of tumor cell differentiation.

Of the numerous substances known in the art to display inhibitory activity on tumor cell proliferation, only a small minority prove to be usable or effective in the treatment of tumors in patients. A major reason for this is the causation of harm also to the normal cells (particularly to the progenitor and stem cells) and the development of intolerable adverse effects. As hedgehog/smoothened signaling is well known to be employed by several normal cell types and for the maintenance of stem cells (Zhang Y et al (2001) Nature 410:599-604), use of cyclopamine on tumors of patients would have been anticipated to lead to adverse effects, especially on the normal tissues around tumors that are exposed to the same schedule and doses of cyclopamine as the tumors. However, treatment with cyclopamine under the conditions described in US 2004/0072914 A1 has not revealed undue adverse effects on normal tissue components (including the putative stem cells) by histological/immunohistochemical criteria. Moreover, former skin sites of cyclopamine application that have been followed up more than 31 months at the time of this writing continue to display healthy-looking normal skin and hair, suggesting functional preservation as well of the stem cells and long-term safety. Our finding that a transient exposure to cyclopamine can suffice for the causations of tumor cell differentiation and apoptosis is further surprising and facilitates treatment of internal tumors as well. We describe in US 2004/0072914 A1 that tumor cells can be caused to undergo apoptosis and/or differentiation in vivo much faster than normal tissue cells so that during the same period of exposure to cyclopamine relatively much smaller proportion or no normal tissue cells undergo cyclopamine-induced apoptosis and/or differentiation, making thereby the clinically detectable or intolerable adverse effects minimal or nonexistent. It is also clear that the therapeutic effectiveness described in US 2004/0072914 A1 and the rapid disappearance of treated tumors could not be possible without the causation of tumor cell apoptosis since merely inhibiting or slowing the tumor cell proliferation by cyclopamine would, at best, help one only to keep the tumor at its pre-treatment size.

Exemplary of the present invention a pigmented nevus on the face of a 82 year old man was found to show rapid decrease of size and decrease of pigmentation following exposure to concentrations of cyclopamine lower than 18 mM (US 2004/0072914 A1, [0049] and FIGS. 6A, 6B). The nevus was located nearby a trichoepithelioma which had been treated by topical applications directly onto the trichoepithelioma of about 25 microliter quantities of a cream preparation having 18 mM cyclopamine. Thus, a relatively lower concentration of cyclopamine reaching to the nevus by diffusion from the nearby direct application area was found to cause a decrease of pigmentation of a hyperpigmented skin lesion within only 24 hours. Applications of the same cream preparation having 18 mM cyclopamine directly onto melanocytic nevi in another subject was found to cause similarly rapid depigmentation and disappearance of the melanocytic nevi.

Thus, the invention is suitable for cosmetic purposes, e.g. decreasing pigmentation in the hyperpigmented skin areas and lesions and improving the appearance of such skin areas.

For topical applications, cyclopamine can be dissolved in ethanol or another suitable solvent and mixed with a suitable base cream, ointment or gel. Cyclopamine may also be entrapped in hydrogels or in other pharmaceutical forms enabling controlled release and may be adsorbed onto dermal patches. In a pharmaceutical composition for topical administration, the cyclopamine or a salt or derivative thereof should be present in a concentration of 0.001 mM to 100 mM, for instance 12 to 24 mM.

An example is a cream preparation obtained by mixing a solution of cyclopamine in ethanol with a base cream, so as to get a final concentration of 18 mM cyclopamine in cream. The base cream used is made predominantly of heavy paraffin oil (10% w/w), vaseline (10% w/w), stearyl alcohol (8% w/w), polyoxysteareth-40 (3% w/w) and water (68% w/w), but another suitably formulated base cream is also possible. Optimal concentration of cyclopamine in a pharmaceutical form as well as the optimal dosing and application schedules can be determined by following well known published optimization methods. Preservation of the undifferentiated cells in the normal epidermis and in hair follicles following exposure to cyclopamine, as described in US 2004/0072914 A1, provide information about the tolerable doses in other possible modes of administration as well.

It is specifically contemplated that molecules can be derived from cyclopamine or synthesized in such a way that they possess structural features to exert similar receptor binding properties and biological/therapeutic effects as cyclopamine. Such a molecule may be called a "derivative of cyclopamine" and defined as follows: A molecule that contains the group of atoms of the cyclopamine molecule required for the binding of cyclopamine to its biological target but contains also modifications of the parent cyclopamine molecule in such ways that the newly derived molecule continues to be able to bind specifically to the same biological target to exert the biological effects of cyclopamine disclosed herein. Such modifications of cyclopamine may include one or more permissible replacement of or a deletion of a molecular group in the cyclopamine molecule or addition of a molecular group (particularly a small molecular group such as the methyl group) to the cyclopamine molecule, provided that the resultant molecule is stable and possesses the capability of specific binding to the same biological target as cyclopamine to exert the biological effects described herein. Derivation of such new molecules from cyclopamine can be readily achieved by those skilled in the art and the possession or lack of the biological effects of cyclopamine in the newly derived molecule can also be readily determined by those skilled in the art by testing for the biological effects disclosed herein.

The invention claimed is:

1. A method for causing decrease of pigmentation in hyperpigmented skin areas of a human, comprising
administration of cyclopamine or another compound that selectively inhibits Hedgehog/Smoothened signaling,
wherein said administration is in a dosage that provides decrease of pigmentation in said skin areas.

2. A method according to claim 1, wherein cyclopamine or said compound is applied in a cosmetic formulation.

3. A method according to claim 1, wherein said compound binds to the same biological target as cyclopamine.

4. A method, for causing decrease of pigmentation in hyperpigmented skin areas of a human, comprising
administration of cyclopamine or another compound that binds to the same biological target as cyclopamine to inhibit Hedgehog/Smoothened signaling,
wherein said compound is applied in a cosmetic formulation and in a dosage that provides decrease of pigmentation in said skin areas.

* * * * *